United States Patent [19]

Temple, Jr. et al.

[11] 4,367,335

[45] Jan. 4, 1983

[54] THIAZOLIDINYLALKYLENE PIPERAZINE DERIVATIVES

[75] Inventors: Davis L. Temple, Jr.; Richard E. Yeager, both of Evansville, Ind.

[73] Assignee: Mead Johnson & Company, Evansville, Ind.

[21] Appl. No.: 289,352

[22] Filed: Aug. 3, 1981

[51] Int. Cl.$^3$ .......................................... C07D 417/06
[52] U.S. Cl. .................................... 544/295; 544/364; 544/369; 424/250; 424/251
[58] Field of Search ........................ 544/369, 364, 295

[56] References Cited

U.S. PATENT DOCUMENTS

| | | | |
|---|---|---|---|
| 2,672,460 | 3/1954 | Conroy | 260/256.4 |
| 2,748,125 | 5/1956 | Hofmann | 260/256.5 |
| 3,398,151 | 8/1968 | Wu | 260/268 |
| 3,717,634 | 2/1973 | Wu | 260/256.4 |
| 3,822,266 | 7/1974 | Edenhofer | 260/268 R |
| 3,857,845 | 12/1974 | Palazzo | 260/268 |
| 3,919,230 | 11/1975 | Hill | 260/256.4 |
| 3,940,398 | 2/1976 | Wade | 260/268 |
| 3,941,789 | 3/1976 | Renth | 260/268 |
| 3,976,776 | 8/1976 | Wu | 424/251 |
| 4,001,237 | 1/1977 | Partyka | 260/256.4 |
| 4,017,622 | 4/1977 | Minami | 424/250 |
| 4,026,894 | 5/1977 | Winn | 260/256.4 |
| 4,029,790 | 6/1977 | Mauvernay | 424/250 |
| 4,060,526 | 11/1977 | Shetty | 260/268 |
| 4,060,615 | 11/1977 | Matier | 424/251 |
| 4,078,063 | 3/1978 | Lumma | 424/250 |
| 4,101,548 | 7/1978 | Crenshaw | 544/284 |
| 4,112,092 | 9/1978 | Regnier | 424/250 |
| 4,138,561 | 2/1979 | Crenshaw | 544/284 |
| 4,161,595 | 7/1979 | Kaplan | 544/284 |
| 4,182,763 | 1/1980 | Casten | 424/251 |
| 4,196,206 | 4/1980 | Molnar | 424/250 |
| 4,216,216 | 8/1980 | Weber | 424/251 |
| 4,267,178 | 5/1981 | Regnier | 424/250 |

FOREIGN PATENT DOCUMENTS 2023594  1/1980  United Kingdom ............... 424/250

OTHER PUBLICATIONS

Wu et al., J. Med. Chem. 12, 876 (1969).
Wu et al., J. Med. Chem. 15, 477 (1972).
Jones et al., J. Chem. Soc., London, 91, (1946).

*Primary Examiner*—Robert Gerstl
*Attorney, Agent, or Firm*—Robert H. Uloth; Robert E. Carnahan

[57] ABSTRACT

Piperazinyl derivatives containing a 3-alkylene-2,4-thiazolidinedione heterocyclic component with relatively selective psychotropic properties are disclosed. The compound 3-[4-[4-(2-pyrimidinyl)-1-piperazinyl]-butyl]-2,4-thiazolidinedione which has selective anxiolytic activity constitutes a typical embodiment of the invention.

14 Claims, No Drawings

THIAZOLIDINYLALKYLENE PIPERAZINE DERIVATIVES

BACKGROUND OF THE INVENTION

This invention generally pertains to heterocyclic carbon compounds having drug and bio-affecting properties and to their preparation and use. In particular, the invention is concerned with 1,4-disubstituted piperazine derivatives wherein the substituents are 2,4-thiazolidinedione-3-alkylenyl and aryl radicals as illustrated by the compound 3-[4-[4-(2-pyrimidinyl)-1-piperazinyl]-butyl]-2,4-thiazolidinedione.

Thiazolidinediones are known to the art. For example, Jones, et al., J. Chem. Soc., London, 91–92 (1946) refer to 5,5-dialkyl-2,4-thiazolidinedione barbituric acid analogs and disclose that an analogous spirothiazolidinedione (1) produced narcosis and analgesia in mice.

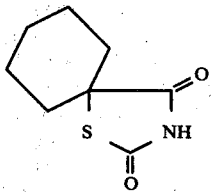

Various types of 1,4-substituted piperazine derivatives are also known to the art as illustrated in the following references.

Great Britain Application No. 2,023,594A discloses 1-(R-alkyl)-4-(3-trifluoromethylthiophenyl)piperazines useful for treating anxiety and depression having general formula (2)

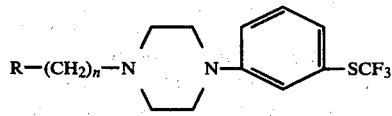

wherein n is 1–3 and R inter alia represents heterocycles such as

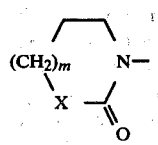

wherein m is 0 or 1 and X is a —S—, —O—, imino, alkyl-imino or methylene.

Wu, U.S. Pat. No. 3,398,151, Wu, et al., U.S. Pat. No. 3,717,634 and, respective, corresponding Wu, et al., publications—J. Med. Chem., 12, 876–881 (1969), 15, 477–479 (1972)—variously describe psychotropic compounds resembling formula (3)

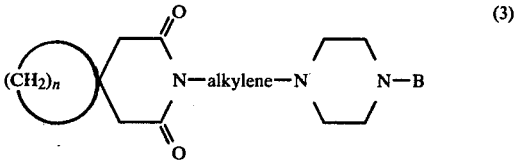

wherein n is 4 or 5 and B inter alia represents phenyl plus various heterocycles (all with optional substituents):

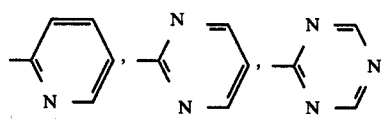

Casten, et al., U.S. Pat. No. 4,182,763 concerns the anxiolytic use of compound (4) which is referred to in the biological literature as buspirone.

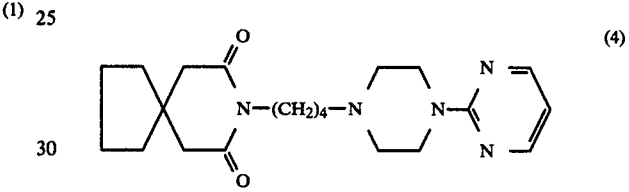

Palazzo, U.S. Pat. No. 3,857,845 describes the compound (5) as having typical tranquilizing properties.

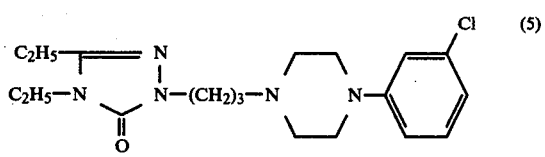

None of the aforementioned references disclose or suggest piperazine derivatives containing the 2,4-thiazolidinedione heterocyclic component of the subject compounds of this invention.

SUMMARY OF THE INVENTION AND DESCRIPTION OF PREFERRED EMBODIMENTS

In its broadest aspect, the present invention is concerned with thiazolidinediones characterized by Formula I

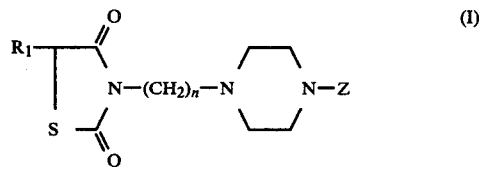

wherein $R_1$ is lower alkyl, n is the integer 2 through 5, Z is a $R_2$-substituted phenyl radical having the formula

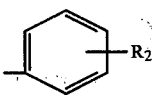

in which $R_2$ is hydrogen, halogen, lower alkyl, lower alkoxy or trifluoromethyl, with the proviso that when n is 3, 4, or 5, Z is also 2-pyrimidinyl or a $R_3$-substituted 2pyridinyl radical having the formula

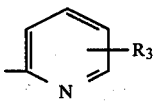

in which $R_3$ is hydrogen or cyano or a pharmaceutically acceptable non-toxic acid addition salt thereof.

It is to be understood that, as used herein, halogen comprehends fluorine, bromine, iodine and preferably chlorine with the terms "lower alkyl" and "lower alkoxy" referring to both straight and branched chain carbon radicals of from 1 to 4 carbon atoms inclusive. Illustrative of these radicals are carbon chains which can be methyl, ethyl, propyl, isopropyl, 1-butyl, 1-methylpropyl and 2-methylpropyl.

The pharmaceutically acceptable acid addition salts of the invention are those in which the anion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation such as solubility, lack of hygroscopicity, compressibility with respect to tablet formation and compatibility with other ingredients with which the substance may be used for pharmaceutical purposes. The salts are routinely made by admixture of the base of Formula I with the selected acid preferably by contact in solution employing an excess of commonly used inert solvents such as water, ether, benzene, ethanol, ethyl acetate and preferably acetonitrile. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include sulfuric, phosphoric, hydrochloric, hydrobromic, hydroiodic, citric, acetic, benzoic, cinnamic, mandelic, phosphoric, nitric, mucic, isethionic, palmitic, heptanoic, and others.

According to the present invention, general embodiments of the process for preparing compounds characterized by Formula I are illustrated by the following reaction schemes.

Method A

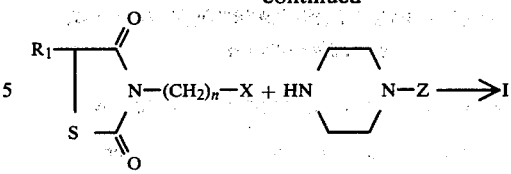

Method B

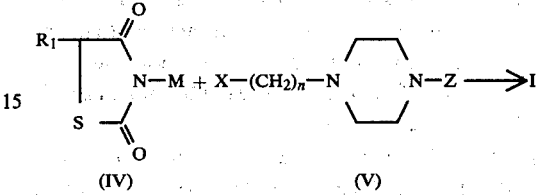

In the foregoing (II-V) formulas, the symbols "$R_1$", "n" and "Z" are as defined above with respect to Formula I with "X" representing the acid residue of a reactive ester grouping such as chloride, bromide, iodide, fluoride, sulfate, phosphate, tosylate or mesylate. The symbol "M" represents an alkali metal salt of the thiazolidinedione, preferably sodium or potassium.

Method A is conventionally carried out under reaction conditions employed in preparing tertiary amines by alkylating secondary amines. Thus, the compounds of Formula I are obtained by reacting a 3-(X-alkylene)-2,4-thiazolidinedione of Formula (II) in an inert reaction medium at temperatures of from about 50° to about 200° C. with a Formula (III) "Z-piperazine" in the presence of a base suitable for use as an acid binding agent. Operable inorganic and organic acid binding bases include tertiary amines, alkali and alkaline earth metal carbonates, bicarbonates, or hydrides with sodium carbonate and potassium carbonate particularly preferred. As referred to herein, the term "inert reaction medium" is meant any protic or aprotic solvent or diluent which does not enter into the reaction to any substantial degree. In this regard, acetonitrile is a particularly preferred solvent with the reaction conveniently carried out at reflux temperature. Satisfactory yields of the present compounds are obtained with reaction periods ranging from about 2-24 hours. Formula (I) products may be purified by crystallization techniques from standard solvent media such as acetonitrile, isopropanol, ethanol and the like and by other conventional methods such as chromatography employing a silica gel column with mixtures of chloroform and alkanols such as methanol and ethanol as eluant.

Method B illustrates another modification of the instant process for preparation of Formula I compounds. In this method, a thiazolidine alkali metal salt (IV) is reacted with a piperazinylalkylene halide or ester of Formula (V). Standard laboratory procedures are employed in carrying out this reaction such as those described for the alkylation step of the Gabriel synthesis—S. Gabriel, Ber. 20, 2224 (1887). In the present case, for instance, the reactants are combined in an inert reaction medium at temperatures ranging from 20° C. to 200° C. Toluene and xylene are particularly preferred solvents for carrying out the reaction but other solvents which do not adversely affect the reaction or reactants can be employed. In this regard, solvents such as dioxane, benzene, dimethylformamide, acetone, acetonitrile, n-butanol and the like are operable. In general, the alkali metal salts (IV) are prepared by treating the corresponding thiazolidinedione with an alkali hydride such as sodium hydride, an alkali alcoholate such as sodium ethoxide, an alkali amide such as sodium amide, or alkali base such as sodium hydroxide or potassium hydroxide in a suitable solvent.

With respect to reactants (II–V), many are known compounds available from commercial sources or can be prepared in accordance with standard synthetic procedures. For example, thiazolidinedione intermediates required for preparation of the thiazolidinedione reactants of Formula (II) are obtained in a manner analogous to that described by E. R. H. Jones, et al., J. Chem. Soc., London, 91–92 (1946). Conversion of the thiazolidinedione to the alkali metal salt (IV) as described above and alkylation with X—$(CH_2)_n$—X wherein "n" and "X" are as defined above in a reaction inert medium such as dimethylformaide affords the 3-(X-alkylene)-2,4-thiazolidinedione (II).

Appropriate piperazine reactants (III) and (V) for Methods A and B are obtained in accordance with standard synthetic procedures employed by those skilled in the art for preparation of similar type compounds. C. B. Pollard, et al., J. Org. Chem., 24, 764–767 (1959), Plazzo, et al. U.S. Pat. No. 3,381,009 and Wu, et al., U.S. Pat. No. 3,717,634 all describe methods applicable for the preparation of such compounds and the aforementioned patents are incorporated herein by reference.

The foregoing general embodiments illustrated by Methods A and B constitute a unitary process for preparing compounds of Formula (I) which comprises reacting a thiazolidinedione of Formula (VI)

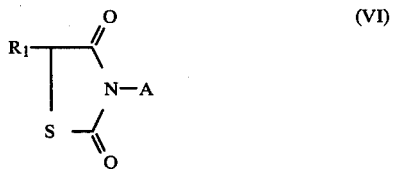

with a piperazine of Formula (VII)

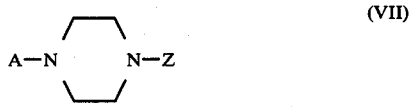

wherein A is independently and appropriately hydrogen, an alkali metal salt or the radical X—$(CH_2)_n$—and the symbols "n, X, and Z" are as defined above.

The Formula (I) compounds are useful pharmacological agents with psychotropic properties. In this regard, they exhibit selective central nervous system activity at non-toxic doses and as such are useful as anxiolytic and/or neuroleptic (antipsychotic) agents. That is to say they produce certain responses in standard in vivo and in vitro pharmacological test systems known to correlate well with relief of anxiety and symptoms of acute and chronic psychosis in man. The following are illustrative of such conventional in vivo test systems used to classify and differentiate a psychotropic agent from a nonspecific CNS depressant and determine potential side-effect liabilities.

| Behavioral Test | Reference |
|---|---|
| Suppression of conditioned avoidance response (CAR) | Albert, Pharmacologist, 4, 152 (1962); Wu et al., J. Med. Chem., 12, 876–881 (1969). |
| Catalepsy | Costall, et al., Psychopharmacologia, 34, 233–41 (1974); Berkson, J. Amer. Statist. Assoc., 48, 565–599 (1953). |
| Fighting Mouse | Tedeschi, et al., J. Pharmacol. Expt. Therap., 125, 28 (1959). |
| Rotarod | Kinnard, et al., J. Pharmacol. Expt. Therap., 121, 354 (1957). |

As further indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of a compound's ability to affect corresponding central nervous system function or cause side effects in vivo. This principal is employed in the following assays which are given by way of example.

| Receptor Binding Assay | Reference |
|---|---|
| Dopamine | Burt, et al., Molec. Pharmacol., 12, 800 (1976); Science, 196, 326 (1977); Creese, et al, Science, 192, 481 (1976). |
| Cholinergic | Yamamura, et al., Proc. Natn. Acad. Sci. USA 71 1725 (1974). |
| Alpha-receptor | Crews, et al., Science 202: 322 (1978). Rosenblatt, et al., Brain Res. 160: 186 (1979) U'Prichard, et al., Science 199: 197 (1978). U'Prichard, et al., Molec. Pharmacol. 13: 454 (1977). |
| Serotonin Type 2 | Peroutka and Snyder, Molec. Pharmacol. 16: 687 (1979). |

According to the pharmacological established by the aforementioned tests, the instant compounds of Formula (I) have promising anxiolytic and/or antipsychotic potential. Regarding selective anxiolytic activity, 3-[4-[4-(2-pyrimidinyl)-1-piperazinyl]-butyl]-2,4-thiazolidinedione and 3-[3-[4-[3-(triflouromethyl)]-phenyl]-1-piperazinyl]-2,4-thiazolidinedione are particularly preferred compounds in that CAR is suppressed in the art without significant dopamine receptor binding activity.

As previously mentioned, the instant compounds have psychotropic properties particularly suited to their use as anxiolytic or neuroleptic agents. Thus, another aspect of the instant invention concerns a process for ameliorating an anxiety or psychotic state in a mammal in need of such treatment which comprises systemic administration to said mammal an effective dose of from about 0.01 to 40 mg/kg body weight of a Formula (I) compound or a pharmaceutically acceptable acid addition salt thereof.

The term systemic administration as used herein refers to oral, rectal, and parenteral (i.e., intramuscular, intravenous, and subcutaneous) routes. Generally, it will be found that when a compound of the present invention is administered orally which is the preferred route, a larger quantity of the active agent is required to produce the same effect as a smaller quantity given parenterally. In accordance with good clinical practice, it is preferred to administer the instant compounds at a concentration level that will produce effective anxiolytic or neuroleptic (antipsychotic) effects without causing any harmful or untoward side effects.

Therapeutically, the instant compounds are generally given as pharmaceutical compositions comprised of an effective anxiolytic or antipsychotic amount of a compound of Formula I or a pharmaceutically acceptable acid addition salt thereof and a pharmaceutically acceptable carrier. Pharmaceutical compositions which provide from about 1 to 500 mg. of the active ingredient per unit dose are preferred and are conventionally prepared as tablets, lozenges, capsules, powders, aqueous or oily suspensions, syrups, elixirs and aqueous solutions.

Preferred oral compositions are in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propylene glycol, and polyethyleneglycols or mixtures thereof. The polyethyleneglycols consist of a mixture of non-volatile, normally liquid, polyethyleneglycols which are soluble in both water and organic liquids and which have molecular weights of from about 200 to 1500.

The following non-limiting examples serve to illustrate preparation of specific compounds of the instant inventions.

EXAMPLE 1

3-[4-[4-[3-(Trifluoromethyl)phenyl]-1-piperazinyl]butyl]-2,4-thiazolidinedione Dihydrochloride (Ia, $R_1$=H, n=4, Z=3-trifluoromethylphenyl)

(a) 2,4-Thiazolidinedione sodium salt 2,4-Thiazolidinedione (11.71 g., 0.1 mole) and 100 ml. of 0.1 N sodium hydroxide (0.1 mole) are mixed and warmed as necessary to effect solution. Concentration of the basic solution under reduced pressure affords a semi-solid which, with repeated acetone trituration and removal of solvent in vacuo, provides a crystalline solid. This material is collected, washed with acetone, and dried at 60° C. in vacuo to provide 15.1 g. (95% yield) of the sodium salt of 2,4-thiazolidinedione, m.p. 225° C. (dec.).

(b) 3-(4-Bromobutyl)-2,4-thiazolidinedione

The 2,4-thiazolidinedione sodium salt (13.91 g., 0.1 mole) is added to a solution of 1,4-dibromobutane (64.77 g., 0.3 mole) in 500 ml. of dry dimethylformamide. After stirring the mixture at room temperature for a 16 hr. period, the resulting clear solution is concentrated in vacuo and residual material dissolved in chloroform, filtered, and concentrated in vacuo to an amber oil. Distillation of the oil affords 20.62 g. (81% yield) of 3-(4-bromobutyl)-2,4-thiazolidinedione, b.p. 105°-115° C. at 0.02 mmHg.

(c)
3-[4-[4-[3-(Trifluoromethyl)phenyl]-1-piperazinyl]butyl]-2,4-thiazolidinedione Dihydrochloride A mixture of 3-(4-bromobutyl)-2,4-thiazolidinedione (2.52 g., 0.01 mole), 1-(3-trifluoromethylphenyl)-piperazine (2.30 g., 0.01 mole), potassium carbonate (1.52 g., 0.011 mole), and potassium iodide (0.18 g., 0.0011 mole), in 100 ml. of acetonitrile is heated under reflux for a 16 hr. period. The reaction mixture is cooled, filtered, and concentrated in vacuo to provide an oily residue which is dissolved in acetonitrile and treated with excess ethanolic hydrogen chloride. Alternatively, the residual material is taken up in chloroform, filtered from trace impurities and the solvent removed prior to salt preparation. The resulting hydrochloride salt precipitates as a solid which is collected by filtration and dried in vacuo at 60° C. to afford 3.4 g. (72% yield), m.p. 171°-174° C. of analytically pure 3-[4-[4-[3-(trifluoromethyl)phenyl]-1-piperazinyl]-butyl]-2,4-thiazolidinedione dihydrochloride.

Anal. Calcd. for $C_{18}H_{22}F_3N_3O_2S.2HCl$ (percent): C, 45.58; H, 5.10; N, 8.86. Found (percent): C, 45.72; H, 5.04; N, 9.02.

EXAMPLE 2

(Ib, $R_1$=H, n=4, Z=3-chlorophenyl)

Reaction of 3-(4-bromobutyl)-2,4-thiazolidinedone with 1-(3-chlorophenyl)piperazine according to the procedure of Example 1(c) affords 3-[4-[4-(3-CHLOROPHENYL)-1-PIPERAZINYL]BUTYL]-2,4-THIAZOLIDINEDIONE DIHYDROCHLORIDE, m.p. 177.5°-178° C., from acetonitrile (43% yield). The melting point may vary to some extent and is generally in the range 172°-178° C.

Anal. Calcd. for $C_{17}H_{22}ClN_3O_2S.2HCl$ (percent): C, 46.32; H, 5.49; N, 9.53. Found (percent): C, 46.37; H, 5.40; N, 9.64.

EXAMPLE 3

(Ic, $R_1$=H, n=4, Z=2-methoxyphenyl)

Reaction of 3-(4-bromobutyl)-2,4-thiazolidinedione with 1-(2-methoxyphenyl)piperazine according to the procedure of Example 1(c) affords 3[4-[4-(2-METHOXYPHENYL)-1-PIPERAZINYL]BUTYL]-2,4-THIAZOLIDINEDIONE DIHYDROCHLORIDE, m.p. 211°-213° C., from acetonitrile (53% yield).

Anal. Calcd. for $C_{18}H_{25}N_3O_3S.2HCl$ (percent): C, 49.54; H, 6.24; N, 9.63. Found (percent): C, 49.40; H, 6.24; N, 9.69.

EXAMPLE 4

(Id, $R_1$=H, n=4, Z=2-pyrimidinyl)

Reaction of 3-(4-bromobutyl)-2,4-thiazolidinedione with 1-(2-pyrimidinyl)piperazine according to the procedure of Example 1(c) affords 3-[4-[4-(2-PYRIMIDINYL)-1-PIPERAZINYL]BUTYL]-2,4-THIAZOLIDINEDIONE DIHYDROCHLORIDE, m.p. 184°-188° C., from acetonitrile (47% yield).

Anal. Calcd. for $C_{15}H_{21}N_5O_2S.2HCl$ (percent): C, 44.12; H, 5.68; N, 17.15. Found (percent): C, 43.88; H, 5.58; N, 17.06.

EXAMPLE 5

(Ie, $R_1$=H, n=4, Z=2-pyridinyl)

Reaction of 3-(4-bromobutyl)-2,4-thiazolidinedione with 1-(2-pyridinyl)piperazine according to the procedure of Example 1(c) affords 3-[4-[4-(2-PYRIDINYL)-1-PIPERAZINYL]BUTYL]-2,4-THIAZOLIDINEDIONE DIHYDROCHLORIDE MONOHYDRATE, m.p. 232.5°–236.5° C., from acetonitrile (62% yield).

Anal. Calcd. for $C_{16}H_{22}N_4O_2S \cdot 2HCl \cdot H_2O$ (percent): C, 45.18; H, 6.16; N, 13.17. Found (percent): C, 45.32; H, 6.02; N, 13.58.

EXAMPLE 6

(If, R=H, n=4, Z=3-cyano-2-pyridinyl)

Reaction of 3-(4-bromobutyl)-2,4-thiazolidinedione with 1-(3-cyano-2-pyridinyl)piperazine according to the procedure of Example I(c) affords 2-[4-[4-(2,4-DIOXOTHIAZOLIDIN-3-YL)BUTYL]-1-PIPERAZINYL]PYRIDINE-3-CARBONITRILE DIHYDROCHLORIDE, m.p. 233°–235° C. (dec.), from ethanol (51% yield).

Anal. Calcd. for $C_{17}H_{21}N_5O_2S \cdot 2HCl$ (percent): C, 47.23; H, 5.37; N, 16.20. Found (percent): C, 47.32; H, 5.47; N, 15.85.

EXAMPLE 7

3-[4-[4-(3-Chlorophenyl)-1-piperazinyl[butyl]-5-propyl-2,4-thiazolidinedione Dihydrochloride (Ig, $R_1$=Propyl, n=4, Z=3-chlorophenyl)

(a) 5-(Propyl)-2,4-thiazolidinedione sodium salt 5-(Propyl)-2,4-thiazolidinedione, prepared by condensing 2-bromopentanoic acid with thiourea followed by acid hydrolysis of the resulting imino-compound as described by E. R. H. Jones, et al., supra. and sodium hydroxide provide an 87% yield of 5-(propyl)-2,4-thiazolidinedione sodium salt according to the procedure of Example I(a).

(b) 5-Propyl-3-(4-bromobutyl)-2,4-thiazolidinedione

The sodium salt of 5-(propyl)-2,4-thiazolidinedione (1.59 g., 0.0088 mole) in 80 ml. of dry dimethylformamide is slowly added to 1,4-dibromobutane (5.68 g., 0.026 mole) in 20 ml. of dry dimethylformamide according to the procedure of Example 1(b) affords a 67% yield of 5-(propyl)-3-(4-bromobutyl)-2,4-thiazolidinedione, b.p. 117°–120° C. at 0.02 mmHg.

(c)
3-[4-[4-(3-Chlorophenyl)-1-piperazinyl]butyl]-5-propyl-2,4-thiazolidinedione Dihydrochloride Reaction of 5-propyl-3-(4-bromobutyl)-2,4-thiazolidinedione (1.48 g., 0.005 mole) with 1-(3-chlorophenyl)-piperazine (1.0 g., 0.005 mole) employing potassium carbonate (1.39 g., 0.01 mole) and potassium iodide (0.18 g., 0.0011 mole) in 100 ml. of acetonitrile according to the procedure of Example 1(c) affords 3-[4-[4-(3-chlorophenyl)-1-piperazinyl]butyl]-5-propyl-2,4-thaizolidine dihydrochloride, m.p. 149°–154° C., from acetonitrile (41% yield).

Anal. Calcd. for $C_{20}H_{28}ClN_3O_2S \cdot 2HCl$ (percent): C, 49.75; H, 6.26; N, 8.70. Found (percent): C, 49.91; H, 6.28; N, 8.82.

EXAMPLE 8

3-[3-[4-(3-Chlorophenyl)-1-piperazinyl]propyl]-2,4-thiazolidinedione Hydrochloride (Ih, $R_1$=H, n=3, Z=3-chlorophenyl)

A mixture of 2,4-thiazolidinedione (4.33 g., 0.037 mole) sodium hydride (1.77 g., 0.037 mole of 50% oil dispersion), in 100 ml. of toluene is refluxed for a 3 hr. period. The resulting solution is cooled to room temperature and a solution of 1-(3-chlorophenyl)-4-(3-chloropropyl)piperazine (10.9 g., 0.037 mole) in 50 ml. of toluene is added. After heating the mixture for a period of approximately 24 hr., the reaction mixture is cooled and filtered. Concentration of the filtrate in vacuo provides the free base as an oil. The hydrochloride salt is prepared by treating a solution of the free base in acetonitrile with excess ethanolic hydrogen chloride and the mixture refrigerated to afford a crystalline solid which is dried in vacuo at 100° C. Crystallization of this material from acetonitrile provides analytically pure 3-[3-[4-(3-CHLOROPHENYL)-1-PIPERAZINYL]-PROPYL]-2,4-THIAZOLIDINEDIONE HYDROCHLORIDE, m.p. 197°–198.5° C.

Anal. Calcd. for $C_{16}H_{20}ClN_3O_2S \cdot HCl$ (percent): C, 49.23; H, 5.42; N, 10.77. Found (percent): C, 48.96; H, 5.51; N, 10.66.

Chromatographic purification of the free base employing a silica gel column with 0–7% ethanol/chloroform eluant and then converting to the hydrochloride provided the title compound, m.p. 197°–199° C.

Anal. Found (percent): C, 49.25; H, 5.26; N, 10.74.

Crystallization of a sample of the hydrochloride salt from isopropanol provided the title compound, m.p. 185°–187° C.

Anal. Found (percent): C, 49.21; H, 5.45; N, 10.84.

Infrared, nuclear magnetic resonance and mass spectrometry spectral data of the aforementioned analyzed lots of the title compound were identical and consistent with the structural features of the title compound.

EXAMPLE 9

(Ii, $R_1$=H, n=3, Z=3-trifluoromethyl)

Reaction of 3-(3-bromopropyl)-2,4-thiazolidinedione with 1-(3-trifluoromethylphenyl)piperazine according to the procedure of Example I(c) affords 3-[3-[4-[3-(TRIFLUOROMETHYL)PHENYL]-1-PIPERAZINYL]-PROPYL]-2,4-THIAZOLIDINEDIONE DIHYDROCHLORIDE, m.p. 185°–188.5° C., from acetonitrile (33% yield).

Anal. Calcd. for $C_{17}H_{20}S_3N_3O_2S \cdot 2HCl$ (percent): C, 44.36; H, 4.82; N, 9.13. Found (percent): C, 44.56; H, 4.87; N, 9.11.

EXAMPLE 10

(Ij, $R_1$=H, n=3, Z=2-methoxyphenyl)

Reaction of 3-(3-bromopropyl)-2,4-thiazolidinedione with 1-(2-methoxyphenyl)piperazine according to the procedure of Example 1(c) affords 3-[3-[4-(2-METHOXYPHENYL)-1-PIPERAZINYL]-PROPYL]-2,4-THIAZOLIDINE-DIONE DIHYDROCHLORIDE HEMIHYDRATE, m.p. 218°–220° C., from acetonitrile (53% yield).

Anal. Calcd. for $C_{17}H_{23}N_3OS \cdot 2HCl \cdot \frac{1}{2}H_2O$ (percent): C, 47.33; H, 6.08; N, 9.74. Found (percent): C, 47.31; H, 5.98; N, 9.50.

EXAMPLE 11

(Ik, $R_1$=H, n=3, Z=2-pyrimidinyl)

Reaction of 3-(3-bromobutyl)-2,4-thiazolidinedione with 1-(2-pyrimidinyl)piperazine according to the procedure of Example 1(c) affords 3-[3-[4-(2-PYRIMIDINYL)-1-PIPERAZINYL]PROPYL]-2,4-THIAZOLIDINEDIONE HYDROCHLORIDE, m.p. 249.5°–251.5° C., from acetonitrile (26% yield).

Anal. Calcd. for $C_{14}H_{19}N_5O_2S \cdot HCl$ (percent): C, 46.99; H, 5.63; N, 19.57. Found (percent): C, 46.87; H, 5.65; N, 19.28.

EXAMPLE 12

(Il, $R_1$=H, n=3, Z=3cyano-2-pyridinyl)

Reaction of 3-(3-bromopropyl)-2,4-thiazolidinedione with 1-(3-cyano-2-pyridinyl)piperazine according to the procedure of Example 1(c) affords 2-[4-[3-(2,4-DIOXOTHIAZOLIDIN-3-YL)PROPYL]-1l-PIPERAZINYL]PYRIDINE-3-CARBONITRILE DIHYDROCHLORIDE, m.p. 197°–201° C., from ethyl acetate (26% yield).

Anal. Calcd. for $C_{16}H_{19}N_5O_2S \cdot 2HCl$ (percent): C, 45.93; H, 5.06; N, 16.74. Found (percent): C, 45.66; H, 4.99; N, 16.53.

EXAMPLE 13

(Im, $R_1$=H, n=2, Z=3-chlorophenyl)

Reaction of 3-(2-bromoethyl)-2,4-thiazolidinedione with 1-(3-chlorophenyl)piperazine according to the procedure of Example 1(c) affords 3-[2-[4-(3-CHLOROPHENYL)-1-PIPERAZINYL]ETHYL]-2,4-THIAZOLIDINEDIONE HYDROCHLORIDE, m.p. 210°–213° C., from ethanol (43% yield).

Anal. Calcd. for $C_{15}H_{18}ClN_3O_2S \cdot HCl$ (percent): C, 47.88; H, 5.09; N, 11.17. Found (percent): C, 47.66; H, 5.21; N, 10.99.

EXAMPLE 14

(In, $R_1$=H, n=3, Z=3-methylphenyl)

Reaction of 3-(3-bromopropyl)-2,4-thiazolidinedione with 1-(3-methylphenyl)piperazine according to the procedure of Example 1(c) affords 3-[3-[4-(3-METHYLPHENYL)-1-PIPERAZINYL]PROPYL]-2,4-THIAZOLIDINEDIONE.

What is claimed is:

1. A thiazolidinedione having Formula I

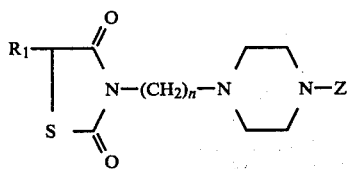

(I)

wherein $R_1$ is hydrogen or lower alkyl of 1 to 4 carbon atoms, n is the integer 2 through 5, Z is a $R_2$-substituted phenyl radical having the formula

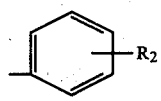

in which $R_2$ is hydrogen, halogen, lower alkyl of 1 to 4 carbon atoms, lower alkoxy of 1 to 4 carbon atoms or trifluoromethyl, with the proviso that when n is 3, 4 or 5, Z is also 2-pyrimidinyl or a $R_3$-substituted 2-pyridinyl radical having the formula

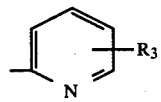

in which $R_3$ is hydrogen or cyano or a pharmaceutically acceptable non-toxic acid addition salt thereof.

2. The compound of claim 1 which is 3-[4-[4-[3-(trifluoromethyl)phenyl]-1-piperazinyl]butyl]-2,4-thiazolidinedione or a pharmaceutically acceptable acid addition salt thereof.

3. The compound of claim 1 which is 3-[4-[4-(3-chlorophenyl)-1-piperazinyl]butyl]-2,4-thiazolidinedione or a pharmaceutically acceptable acid addition salt thereof.

4. The compound of claim 1 which is 3-[4-[4-(2-methoxyphenyl)-1-piperazinyl]butyl]-2,4-thiazolidinedione or a pharmaceutically acceptable acid addition salt thereof.

5. The compound of claim 1 which is 3-[4-[4-(2-pyrimidinyl)-1-piperazinyl]butyl]-2,4-thiazolidinedione or a pharmaceutically acceptable acid addition salt thereof.

6. The compound of claim 1 which is 3-[4-[4-(2-pyridinyl)-1-piperazinyl]butyl]-2,4-thiazolidinedione or a pharmaceutically acceptable acid addition salt thereof.

7. The compound of claim 1 which is 2-[4-[4-(2,4-dioxothiazolidin-3-yl]butyl]-1-piperazinyl]pyridine-3-carbonitrile or a pharmaceutically acceptable acid addition salt thereof.

8. The compound of claim 1 which is 3-[4-[4-(3-chlorophenyl)-1-piperazinyl]butyl]-5-propyl-2,4-thiazolidinedione or a pharmaceutically acceptable acid addition salt thereof.

9. The compound of claim 1 which is 3-[3-[4-(3-chlorophenyl)-1-piperazinyl]propyl]-2,4-thiazolidinedione or a pharmaceutically acceptable acid addition salt thereof.

10. The compound of claim 1 which is 3-[3-[4-[3-(trifluoromethyl)phenyl]-1-piperazinyl]propyl]-2,4-thiazolidinedione or a pharmaceutically acceptable acid addition salt thereof.

11. The compond of claim 1 which is 3-[3-[4-(2-methoxyphenyl)-1-piperazinyl]propyl]-2,4-thiazolidinedione or a pharmaceutically acceptable acid addition salt thereof.

12. The compound of claim 1 which is 3-[3-[4-(2-pyrimidinyl)-1-piperazinyl]propyl]-2,4-thiazolidinedione or a pharmaceutically acceptable acid addition salt thereof.

13. The compound of claim 1 which is 2-[4-[3-(2,4-dioxothiazolidin-3-yl)propyl-1-piperazinyl]pyridine-3-carbonitrile or a pharmaceutically acceptable acid addition salt thereof.

14. The compound of claim 1 which is 3-[2-[4-(3-chlorophenyl)-1-piperazinyl]ethyl]-2,4-thiazolidinedione or a pharmaceutically acceptable acid addition salt thereof.

* * * * *